(12) United States Patent
Chen et al.

(10) Patent No.: US 10,806,557 B1
(45) Date of Patent: Oct. 20, 2020

(54) TISSUE SCAFFOLDING DEVICES, METHODS OF USING, AND METHODS OF MAKING

(71) Applicant: Microfabrica Inc., Van Nuys, CA (US)

(72) Inventors: Richard T. Chen, Stevenson Ranch, CA (US); Eric C. Miller, Los Gatos, CA (US)

(73) Assignee: Microfabrica Inc., Van Nuys, CA (US)

( * ) Notice: Subject to any disclaimer, the term of this patent is extended or adjusted under 35 U.S.C. 154(b) by 440 days.

(21) Appl. No.: 15/647,243

(22) Filed: Jul. 11, 2017

Related U.S. Application Data

(60) Provisional application No. 62/360,578, filed on Jul. 11, 2016.

(51) Int. Cl.
*A61F 2/00* (2006.01)
*C12N 5/00* (2006.01)

(52) U.S. Cl.
CPC .......... *A61F 2/0077* (2013.01); *C12N 5/0068* (2013.01); *C12N 5/0075* (2013.01); *A61F 2210/0004* (2013.01); *A61F 2210/0014* (2013.01); *A61F 2210/0076* (2013.01); *A61F 2250/0012* (2013.01); *A61F 2250/0067* (2013.01); *A61F 2250/0096* (2013.01)

(58) Field of Classification Search
CPC ... A61F 2/0077; C12N 5/0062; C12N 5/0075; C12N 5/0697
See application file for complete search history.

(56) References Cited

U.S. PATENT DOCUMENTS

| | | |
|---|---|---|
| 5,190,637 A | 3/1993 | Guckel |
| 6,027,630 A | 2/2000 | Cohen |
| 2002/0162791 A1* | 11/2002 | Jacobson ............. A61F 2/00 210/483 |
| 2006/0136182 A1* | 6/2006 | Vacanti ............. C12M 25/14 703/11 |

OTHER PUBLICATIONS

Fergal J. O'Brien, "Biomaterials & scaffolds for tissue engineering", Materials Today journal, Mar. 2011, pp. 88-95, vol. 14—No. 3, Elsevier.
Jia An, et al., "Design and 3D Printing of Scaffolds and Tissues", Engineering journal, Jun. 2015, pp. 261-268, vol. 1—Issue 2, Elsevier.

* cited by examiner

*Primary Examiner* — Leslie Lopez
(74) *Attorney, Agent, or Firm* — Dennis R. Smalley

(57) ABSTRACT

Embodiments of the present invention are directed to microscale and millimeter scale tissue scaffolding structures that may be static or expandable and which may be formed of biocompatible metals or other materials that may be coated to become biocompatible. Scaffold structures may include features for holding desired biological or physiological materials to enhance selected tissue growth. Scaffolding devices may be formed by multi-layer, multi-material electrochemical fabrication methods.

17 Claims, 17 Drawing Sheets

As expanded

As expanded

Build Axis = Z

As contracted and possibly as formed

As expanded

As contracted and possibly as formed

As expanded

As contracted and possibly as formed

As expanded

As contracted and possibly as formed

As expanded

As contracted and possibly
as formed

Hinges

As expanded

As contracted and possibly as formed

As expanded

Cut view
As expanded

Build Axis = Z

As contracted and possibly
as formed

Connected Cells

Independent Cells

TISSUE SCAFFOLDING DEVICES, METHODS OF USING, AND METHODS OF MAKING

RELATED APPLICATIONS

This application claims benefit of U.S. Provisional Patent Application No. 62/360,578, filed Jul. 11, 2016. This referenced application as well as all other patents and applications referenced herein are incorporated herein by reference.

FIELD OF THE INVENTION

Embodiments of the present invention relate to tissue scaffolding structures for use in supporting in vitro or in vivo tissue growth where the structures have (1) similar build and use sizes, (2) one or more elements that can allow the structure to expand from a build size, or placement size (which may be larger or smaller than the build size) to a larger functional size after placement or insertion into a tissue growth site by one or more of (1) technician or surgeon manipulation prior to tissue growth, (2) as a result of the tissue growth itself, and/or (3) as a result releasing a biasing force (e.g. a tensioned spring, compressed spring, a rotary spring, manipulation of a shape memory alloy, or the like). In some embodiments, the scaffolding structures may include drugs or other biochemical or physicochemical materials to add in specific tissue growth or inhibition of specific tissue growth. In still other embodiments, methods for using such structures are provided, while in still others, methods for fabricating such structures are provided. Some fabrication embodiments of the present invention also relate to the field of electrochemical fabrication of multi-layer micro-scale or millimeter scale three dimensional structures, parts, components, or devices where each layer is formed from a plurality of deposited materials.

BACKGROUND OF THE INVENTION

Tissue engineering provides useful benefits in the medical arts for patients that have damaged or non-functional organs or other tissue. Tissue scaffolding structures may be used in tissue engineering to provide a framework of desired configuration and/or of desired functionality that allows or promotes functional tissue growth or the inhibition of undesired tissue growth. A need exists for improved tissue scaffolding structures, improved methods for making such structures, and improved methods for using such structures.

Multi-layer multi-material electrochemical fabrication methods exist that can be used in the batch fabrication of millimeter or microscale structures or devices. Such methods have been and are being commercially pursued by Microfabrica® Inc. (formerly MEMGen Corporation) of Van Nuys, Calif. under the name MICA FREEFORM® (formerly EFAB®).

Various electrochemical fabrication techniques were described in U.S. Pat. No. 6,027,630, issued on Feb. 22, 2000 to Adam Cohen. Some embodiments of this electrochemical fabrication technique allow the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate. While in the presence of a plating solution, a current can be passed to the substrate causing electrodeposition (or even electroetching) in those regions not inhibited by the presence of conformable material. For convenience, these masks might be generically called conformable contact masks; the masking technique may be generically called a conformable contact mask plating process.

Other electrochemical fabrication techniques were described in U.S. Pat. No. 5,190,637 to Henry Guckel. In this patent, selective deposition occurs via a photoresist mask that is formed and patterned on a deposition substrate and is destructively removed after patterned deposition occurs. For convenience, these masks might be generically called adhered masks as they are adhered to the deposition substrate.

Electrochemical deposition processes for forming multi-layer structures may be carried out in a number of different ways. When forming millimeter scale or micro-scale structures on large substrates, multiple structures may be formed simultaneously (i.e. in a batch process) via formation of a first layer of the multiple structures followed by the buildup of successive layers of each structure on previously formed layers. In one form, a basic process involves the execution of three separate operations during the formation of each layer of the structure that is to be formed:

1. Selectively depositing at least one material by electrodeposition upon one or more desired regions of a substrate. Typically this material is either a structural material or a sacrificial material.
2. Next, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.
3. Finally, planarizing the materials deposited during the first and second operations to produce a smoothed surface of a first layer of desired thickness having at least one lateral region containing the at least one material and at least one other lateral region containing at least the one additional material.

As used in this application, and in distinction to the terminology used in the '637 patent, a "layer", a "build layer", "layer or structure", or the like, generally does not refer to the deposition of a single material but to a "multi-material layer" that extends laterally (e.g. in the X and Y directions) and has a vertical region (e.g. in the Z-direction) of desired thickness that is generally sandwiched between successive planarized levels such that the different materials occupy different lateral parts of the layer and with at least one of the materials being a structural material that will form part of the structure once formation is completed. Each layer generally represents a cross-section of a multi-layer structure.

After formation of a layer, one or more successive layers may be formed adjacent to and on an immediately preceding layer and adhered to the smoothed surface of that preceding layer. These additional layers are formed by repeating the first through third operations one or more times wherein the formation of each successive layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

SUMMARY OF THE INVENTION

It is an object of some embodiments of the invention to provide an improved micro-scale or millimeter scale tissue scaffolding device.

It is an object of some embodiments of the invention to provide an improved in vitro tissue scaffolding method.

It is an object of some embodiments of the invention to provide an improved in vivo tissue scaffolding method.

It is an object of some embodiments of the invention to provide an improved method of fabricating tissue scaffolding structures.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

In a first aspect of the invention a microscale, mesoscale, or millimeter scale expandable tissue scaffolding device, includes: (a) at least one first element having a plurality of first side facing features that have a first height and first slots extending at least part way along said height and a joining structure that connects said side facing features; (b) at least one second element having a plurality of second guide features that movably extend into said first slots of said first element, such that movement of the at least one second element relative to the first element is permitted in a direction parallel to the first height, (c) at least one first stop feature forming part of one or both of the first and second elements that engages the other of the first or second elements upon movement of the first and second elements reaching a first limit such that the at least one first stop feature inhibits excess movement and separation of the first and second elements.

Numerous variations of the first aspect of the invention exist and include for example (1) the second element comprising a plurality of second side facing second features that have a second height and second slots extending at least part way along said second height and a joining structure that connects said second side facing features and further including at least one third element having a plurality of second guide features that movably extend into said second slots of said second element, such that movement of the at least one third element relative to the second element is permitted in a direction parallel to the second height; and still further including at least one second stop feature forming part of one or both of the second and third elements that engages the other of the second or third elements upon movement of the second and third elements reaching a second limit such that the at least one second stop feature inhibits excess movement and separation of the second and third elements.

In a second aspect of the invention an in vivo method for treating a patient, includes: (a) providing a microscale, mesoscale, or millimeter scale expandable tissue scaffolding device, including: (i) at least one first element having a plurality of first side facing features that have a first height and first slots extending at least part way along said height and a joining structure that connects said side facing features; (ii) at least one second element having a plurality of second guide features that movably extend into said first slots of said first element, such that movement of the at least one second element relative to the first element is permitted in a direction parallel to the first height; and (iii) at least one first stop feature forming part of one or both of the first and second elements that engages the other of the first or second elements upon movement of the first and second elements reaching a first limit such that the at least one first stop feature inhibits excess movement and separation of the first and second elements; (b) inserting the tissue scaffolding device into a target region in a body of the patient; and (c) allowing selected tissue of the patient to enter and grow inside the an opening in the tissue scaffolding device so as to provide a repair or treatment for the patient.

Numerous variations of the second aspect of the invention exist and include for example (1) the second element of the tissue scaffolding device comprising a plurality of second side facing second features that have a second height and second slots extending at least part way along said second height and a joining structure that connects said second side facing features; and wherein the tissue scaffolding device additionally comprises: at least one third element having a plurality of second guide features that movably extend into said second slots of said second element, such that movement of the at least one third element relative to the second element is permitted in a direction parallel to the second height; and further comprises at least one second stop feature forming part of one or both of the second and third elements that engages the other of the second or third elements upon movement of the second and third elements reaching a second limit such that the at least one second stop feature inhibits excess movement and separation of the second and third elements; (2) the tissue scaffolding device changing shape while material of interest is growing; (3) the tissue scaffolding device is made to change shape from a contracted sized to an expanded size after insertion in to the target region; (4) the tissue scaffolding structure influencing the shape of the tissue growth; (5) the tissue scaffolding structure limiting the shape of the tissue as it grows; (6) the tissue scaffolding device being delivered in contracted form through a small opening, then expanded afterwards via motivation selected from the group consisting of (a) by growth of the tissue of interest, (b) by random movement, and (c) by the a surgeon; (7) windows existing in the sides of scaffold elements that help guide tissue growth; (8) the scaffolding elements including material selected from the group consisting of (a) bio-material that promotes selected material growth, (b) material that provides biocompatibility, (c) material that inhibits tissue growth, (d) material that provides a beneficial treatment for the patient, (e) an bio absorbable material, and (f) an biodegradable material, and (f) a tissue seeding material or material that can aid in the seeding of tissue; (9) the tissue scaffolding device providing structural integrity for the tissue that is growing within it; (10) the tissue scaffolding device further including features selected from the group consisting of (a) one or more anchoring features, (b) one or more locking mechanisms, (c) one or more mechanisms for inhibit contraction of the device after expansion, and (d) one or more barbs to aid in securing the device to a target location; (11) the tissue scaffolding device having features that are optimized to work with bio adhesives; (12) the scaffolding device having at least two different materials that promote growth of different tissues; (13) the tissue scaffolding device being capable of expanding in multiple non-parallel directions; (14) the tissue scaffolding device initially including controllably releasable drugs; (15) at least a portion of the tissue scaffolding device including a metal and being fabricated at least in part using a multi-layer, multi-material electrochemical fabrication process; (16) the tissue scaffolding device including an electronic component, selected from the group consisting of (a) a pressure sensor, (b) a response driven electronic component that is driven by one of pressure, electrical impulse or temperature, (c) an electronic device driven by one of RF, a piezo electric device, electrochemical interaction, or electro-mechanical capacitance or induction, and (d) an electronic component that is operated in response to one of a closed loop or a periodic cycle within the body.

In a third aspect of the invention a method for treating a patient includes: (a) providing a microscale, mesoscale, or millimeter scale expandable tissue scaffolding device, including: (i) at least one first element having a plurality of first side facing features that have a first height and first slots extending at least part way along said height and a joining structure that connects said side facing features; (ii) at least one second element having a plurality of second guide features that movably extend into said first slots of said first element, such that movement of the at least one second element relative to the first element is permitted in a direction parallel to the first height; (iii) at least one first stop feature forming part of one or both of the first and second elements that engages the other of the first or second elements upon movement of the first and second elements reaching a first limit such that the at least one first stop feature inhibits excess movement and separation of the first and second elements; (b) growing tissue within the tissue scaffolding device in an in vitro process; (c) inserting the scaffolding device along with in grown tissue into a target region in a body of the patient; and (d) allowing the body of the patient to incorporate the inserted scaffolding device and grown tissue to provide a repair or treatment for the patient.

In a fourth aspect of the invention a microscale, mesoscale, or millimeter scale tissue scaffolding device, includes a plurality of stacked and laterally offset open cells into which selected tissue can grow, wherein the tissue scaffolding device comprises a plurality of metal layers.

In a fifth aspect of the invention a microscale, mesoscale, or millimeter scale expandable tissue scaffolding device, includes a plurality of elements joined to other elements via slidable channels or guides wherein the set of elements defines a an expandable cell when in a collapsed state and an expanded cell after sliding, wherein the cell is configured to promote tissue growth therein.

In a sixth aspect of the invention a microscale, mesoscale, or millimeter scale expandable tissue scaffolding device includes a plurality of elements joined to other elements via bendable, rotatable or foldable joints wherein each element defines a cell into which tissue can grow and wherein the plurality of elements as a whole define a desired shape when expanded into which tissue is intended to grow.

Other aspects of the invention will be understood by those of skill in the art upon review of the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 8A and 8B provide perspective views of an expandable, substantially rectangular, platform cell that may form a single cell expandable scaffolding device with side walls that fold outward from a collapsed position to an expanded position according to a seventh embodiment of the invention wherein FIG. 8A depicts the device in an expanded state while FIG. 8B depicts the device in a contracted or potentially as formed state.

FIGS. 9A-9C provide perspective views of a three stage, expandable platform stack that may function as a multi-cell expandable tissue scaffolding device according to an eighth embodiment of the invention wherein individual cells are similar to that shown in FIGS. 8A and 8B with the exception that individual cells are separated, or joined, by a rectangular ring structure wherein FIG. 9A shows the device in an expanded state, FIG. 9B shows a cut view of the device in an expanded state, and FIG. 9C shows the device in contracted and possibly as fabricated state.

FIGS. 11A and 11B provide perspective views of a three stage, expandable platform stack that may function as a multi-cell expandable tissue scaffolding device according to an tenth embodiment of the invention wherein individual cells have side walls that fold outward as expansion occurs wherein FIG. 11A shows the device in a contracted, and possibly as fabricated, state, while FIG. 11B shows the device in an expanded state.

DETAILED DESCRIPTION OF PREFERRED EMBODIMENTS

Some embodiments of the invention provide for tissue scaffolding structures or devices that may be formed in a variety of manners. Some such tissue scaffolding devices may be formed in a final use configuration while others may be formed in a manner that allow for compaction of the device volume prior to use (e.g. for insertion) and then expansion upon use. Some such structures or devices may be on the micro-scale, or smaller, while others may be on the millimeter scale or even larger.

Figure 1A:
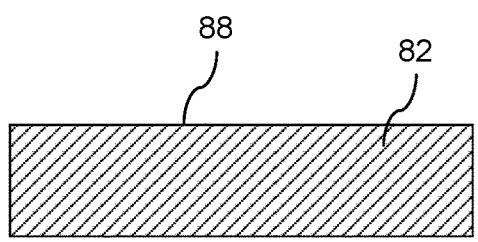
FIGS. 1A-1F schematically depict the formation of a first layer of a structure using adhered mask plating where the blanket deposition of a second material overlays both the openings between deposition locations of a first material and the first material itself.
Figure 1B:
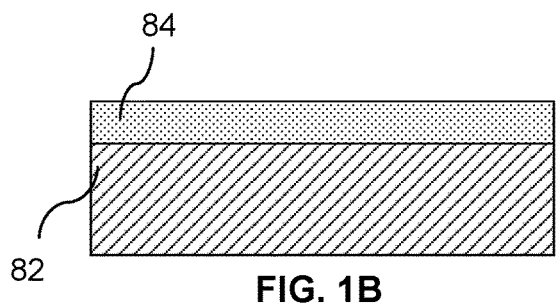
Figure 1C:
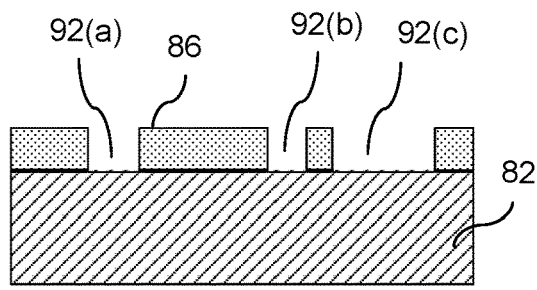
Figure 1D:
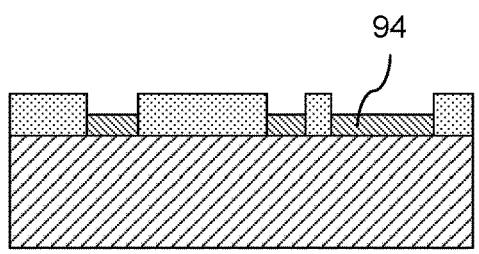
Figure 1E:
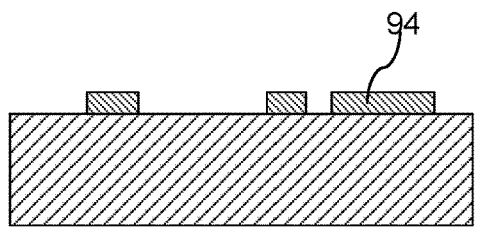
Figure 1F:
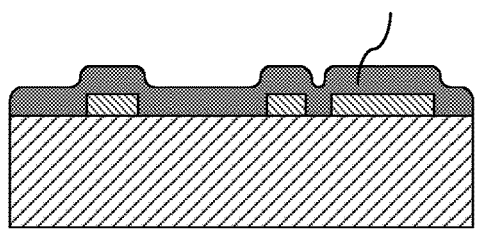
Figure 1G:
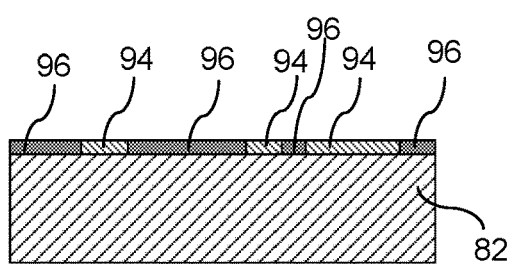
FIG. 1G depicts the completion of formation of the first layer resulting from planarizing the deposited materials to a desired level.
Figure 1H:
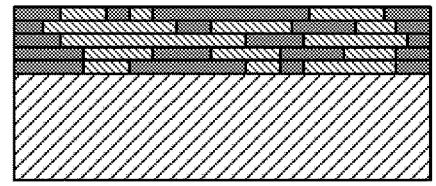
FIGS. 1H and 1I respectively depict the state of the process after formation of the multiple layers of the structure and after release of the structure from the sacrificial material.
Figure 1I:
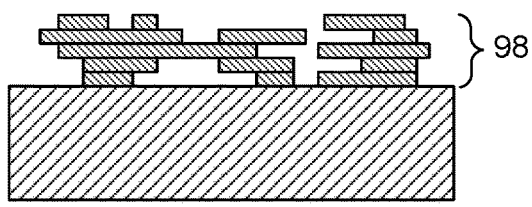

Formation methods for such scaffolds, and particularly for millimeter or microscale scaffolds, may advantageously take the form of multi-layer multi-material electrochemical fabrication methods. An example formation method is set forth in FIGS. 1A-11. FIGS. 1A-11 illustrate side views of various states in a simple adhered mask patterning example of multi-layer, multi-material electrochemical fabrication process. FIGS. 1A-1G illustrate various stages in the formation of a single layer of a multi-layer fabrication process where a second metal is deposited on a first metal as well as in openings in the first metal so that the first and second metal form part of the layer. In FIG. 1A a side view of a substrate 82 having a surface 88 is shown, onto which patternable photoresist 84 is cast as shown in FIG. 1B. In FIG. 1C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 1D a metal 94 (e.g. nickel) is shown as having been electroplated into the openings 92(a)-92(c). In FIG. 1E the photoresist has been removed (i.e. chemically stripped) from the substrate to expose regions of the substrate 82 which are not covered with the first metal 94. In FIG. 1F a second metal 96 (e.g. silver) is shown as having been blanket electroplated over the entire exposed portions of the substrate 82 (which is conductive) and over the first metal 94 (which is also conductive). FIG. 1G depicts the completed first layer of the structure which has resulted from the planarization of the first and second metals down to a height that exposes the first metal and sets a thickness for the first layer. In FIG. 1H the result of repeating the process steps shown in FIGS. 1B-1G several times to form a multi-layer structure is shown where each layer consists of two materials. For most applications, one of these materials is removed as shown in FIG. 1I to yield a desired 3-D structure 98 (e.g. component or device).

Such methods may be enhanced by additional or alternative steps that provide for inclusion of more than one structural material on some layers or different structural materials on different layers. Such methods may be enhanced by providing additional steps that provide for layer-by-layer coatings, or formation of coatings after formation of a plurality of layers and removal of sacrificial material. The additional coatings may provide materials of interest such as dielectrics to selected surfaces, biologically active materials to selected surfaces, texturing to selected surfaces, and/or creation of cavities, reduced layer to layer discontinuities, material interlacing between successive layers. Such enhanced formation methods may be understood with the aid of materials set forth in the various patent applications and patents incorporated herein by reference as well as combinations of teachings set forth in these various applications and patents so long as the combinations do not completely eliminate benefits provided by the individual methods while providing enhanced benefits.

Structures of interest may be formed from a plurality of build layers (e.g. two or more layers, more preferably five or more layers, and most preferably ten or more layers) each including at least two materials (e.g. at least one structural material and at least one sacrificial material). In some embodiments, layer thicknesses may be as small as 0.5 microns or as large as 50 microns. In other embodiments, thinner layers may be used while in other embodiments, thicker layers may be used. In some embodiments microscale structures may be formed that have lateral features positioned with micron level precision (e.g. 0.1 to 10 microns), minimum features size on the order of microns to tens of microns or larger, and with lateral dimensions that are 2 microns or larger. In some embodiments millimeter-scale structures may be formed that have lateral features positioned with millimeter level precision (0.1 to 10 millimeters), minimum features size on the order of 0.1 millimeters or larger, and with lateral dimensions that are 0.2 millimeters or larger. In some embodiments mesoscale structures may be formed with precision, minimum features sizes, and lateral dimensions intermediate to those of the microscale and millimeter scale structures. In other embodiments structures with less precise feature placement, and/or larger minimum features may be formed. In still other embodiments, higher precision and smaller minimum feature sizes may be desirable.

Though non-electroplating methods may be used to form tissue scaffolding devices, some preferred methods involve electrochemical fabrication methods which may use a single patterning technique on all layers or different patterning techniques on different layers. For example, various fabrication method embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). More information about such patterning methods may be found in the various patent applications and patents that are incorporated herein by reference.

Patterning operations may be used in selectively depositing material and/or may be used in the selective etching of material. Selectively etched regions may be selectively filled in or filled in via blanket deposition, or the like, with a different desired material. Substrates upon which layers may be formed may be sacrificed in the build process, they may be reusable, or may even remain attached to formed structures to become part of the structures.

Definitions

This section of the specification is intended to set forth definitions for a number of specific terms that may be useful in describing the subject matter of the various embodiments of the invention. It is believed that the meanings of most if not all of these terms is clear from their general use in the specification but they are set forth hereinafter to remove any ambiguity that may exist. It is intended that these definitions be used in understanding the scope and limits of any claims that use these specific terms. As far as interpretation of the claims of this patent disclosure are concerned, it is intended that these definitions take presence over any contradictory definitions or allusions found in any materials which are incorporated herein by reference.

"Build" as used herein refers, as a verb, to the process of building a desired structure (or part) or plurality of structures (or parts) from a plurality of applied or deposited materials which are stacked and adhered upon application or deposition or, as a noun, to the physical structure (or part) or structures (or parts) formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" or "lateral" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519 now U.S. Pat. No. 7,252,861. This referenced application is incorporated herein by reference as if set forth in full. In most embodiments, a build layer includes at least one primary structural material and at least one primary sacrificial material. However, in some embodiments, two or more primary structural materials may be used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example they may be defined by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). As another example, they may be defined by levels at which process steps or operations are repeated. As still a further example, they may be defined, at least theoretically, as lateral extents of structural material can change to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer height or boundary level). For example, lapping removes material in a substantially non-selective manner though some amount of recession of one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization may be followed or preceded by thermally induced planarization (e.g. melting) or chemically induced planarization (e.g. etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. During release or separation, sacrificial material is typically removed via a chemical etching operation but in some embodiments it may be removed via a melting operation, electrochemical etching operation, laser ablation, or the like. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties therefrom (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural. Sacrificial materials are typically removed by a dissolution process, or the like, that destroys the geometric configuration of the sacrificial material as it existed on the build layers. In many embodiments, the sacrificial material is a conductive material such as a metal thought in some embodiments it may be a dielectric material and even a photoresist material. As will be discussed hereafter, masking materials though typically sacrificial in nature are not termed sacrificial materials herein unless they meet the required definition of sacrificial material.

"Multilayer structures" are structures formed from multiple build layers of deposited or applied materials.

"Multilayer three-dimensional (or 3D or 3-D) structures" are Multilayer Structures wherein the structural material portions of at least two layers are not identical in configuration, not identical in lateral positioning, or not identical in orientation (i.e. the structural materials on the two layers do not completely overlap one another.

"Complex multilayer three-dimensional (or 3D or 3-D) structures" are multilayer three-dimensional structures formed from at least three layers where a line may be defined that hypothetically extends vertically through at least some portion of the build layers of the structure and that extends from structural material through sacrificial material and back through structural material or extends from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one of structural material or void (when the sacrificial material is removed) to the other of void or structural material and then back to structural material or void as the line is traversed along at least a portion of its length.

"Moderately complex multilayer three-dimensional (or 3D or 3-D) structures are complex multilayer 3D structures for which the alternating of void and structure or structure and void not only exists along one of a vertically or horizontally extending line but along lines extending both vertically and horizontally.

"Highly complex multilayer (or 3D or 3-D) structures are complex multilayer 3D structures for which the structure-to-void-to-structure or void-to-structure-to-void alternations occur not only once along the line but also occur a plurality of times along a definable horizontally or vertically extending line.

"Minimum feature size" or "MFS" refers to a necessary or desirable spacing between structural material elements on a given layer that are to remain distinct in the final device configuration. If the minimum feature size is not maintained for structural material elements on a given layer, the fabrication process may result in structural material inadvertently bridging what were intended to be two distinct elements (e.g. due to masking material failure or failure to appropriately fill voids with sacrificial material during formation of the given layer such that during formation of a subsequent layer structural material inadvertently fills the void). More care during fabrication can lead to a reduction in minimum feature size. Alternatively, a willingness to accept greater losses in productivity (i.e. lower yields) can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of gaps or voids (e.g. the MFS for sacrificial material regions when sacrificial material is deposited first). Conversely a minimum feature size for structure material regions (minimum width or length of structural material elements) may be specified. Depending on the fabrication method and order of deposition of structural material and sacrificial material, the two types of minimum feature sizes may be the same or different. In practice, for example, using electrochemical fabrication methods as described herein, the minimum feature size on a given layer may be roughly set to a value that approximates the layer thickness used to form the layer and it may be considered the same for both structural and sacrificial material widths. In some more rigorously implemented processes (e.g. with higher examination regiments and tolerance for rework), it may be set to an amount that is 80%, 50%, or even 30% of the layer thickness. Other values or methods of setting minimum feature sizes may be used. Worded another way, depending on the geometry of a structure, or plurality of structures, being formed, the structure, or structures, may include elements (e.g. solid regions) which have dimensions smaller than a first minimum feature size and/or have spacings, voids, openings, or gaps (e.g. hollow or empty regions) located between elements, where the spacings are smaller than a second minimum feature size where the first and second minimum feature sizes may be the same or different and where the minimum feature sizes represent lower limits at which formation of elements and/or spacing can be reliably formed. Reliable formation refers to the ability to accurately form or produce a given geometry of an element, or of the spacing between elements, using a given formation process, with a minimum acceptable yield. The minimum acceptable yield may depend on a number of factors including: (1) number of features present per layer, (2) number of layers, (3) the criticality of the successful formation of each feature, (4) the number and severity of other factors affecting overall yield, and (5) the desired or required overall yield for the structures or devices themselves. In some circumstances, the minimum size may be determined by a yield requirement per feature which is as low as 70%, 60%, or even 50%. While in other circumstances the yield requirement per feature may be as high as 90%, 95%, 99%, or even higher. In some circumstances (e.g. in producing a filter element) the failure to produce a certain number of desired features (e.g. 20-40% failure may be acceptable while in an electrostatic actuator the failure to produce a single small space between two moveable electrodes may result in failure of the entire device. The MFS, for example, may be defined as the minimum width of a narrow processing element (e.g. photoresist element or sacrificial material element) or structural element (e.g. structural material element) that may be reliably formed (e.g. 90-99.9 times out of 100) which is either independent of any wider structures or has a substantial independent length (e.g. 200-1000 microns) before connecting to a wider region.

Scaffolding device embodiments of the present invention can be grouped into three categories: (1) Scaffolding devices that expand from a compressed or collapsed state to an expanded state by movement of linearly slidable elements moving relative to one another; (2) Scaffolding devices that expand from a contracted or collapsed state to an expanded state by bending or rotation of portions of elements relative to one another; and (3) static or fixed size scaffolds. Of course other embodiments are possible that involve combinations of structures or functionalities associated with two or more of group (1)-(3) devices. For example, some devices may include the ability to expand from a contracted size to an expanded size via a combination of linear motion (e.g. like that found in group 1) and rotary motion (e.g. like that found in group 2).

Group 1 embodiments provide expanding scaffolds via movement of two or more scaffold elements sliding relative to one another. Such scaffolds may be based on a single unit cell that includes multiple slidable elements or on multiple unit cells that may for example be configured into various array configurations that extend laterally or are even stacked one above another. Such lateral spacing and stacking may form arrays with regular or irregular spacing between unit cells. The shape of one unit cell can be hexagonal, square, triangle or any other shape that can nest multiple sliding levels. Each unit cell is made of multiple levels that can move with respect to each other and where movement may be in a direction parallel to a layer stacking direction (for structures made from a plurality of adhered layers), may be perpendicular to a layer stacking direction or at some other orientation relative to a layer stacking direction. Each level of a unit cell may include side elements that are include an open metal frame structure or a closed metal structure (e.g. solid walls). Each unit cell may include top or bottom facing elements (e.g. ceilings or floors) that are defined by open frame structures or closed metal structures. Each successive structural level can preferably nest within, around, or otherwise interlace with adjacent levels either fully or partially (e.g. during formation the levels may nest together to minimum height during fabrication). In some implementations, each successive level can become laterally smaller with respect to a preceding level while in other implementations, each successive level can become laterally larger with respect to a preceding level, while in still other implementations a mixture of these prior two implementations may exist so long as vertical expansion and/or some horizontal translation can occur. In some implementations each successive level may be the same size as the previous level but offset from it. In some implementations, some successive levels may be smaller while others may be larger than preceding levels.

In these size changing slidable scaffolding devices, each level (e.g. element) of the device can slide (e.g. move vertically, horizontally or in some diagonal direction) with respect to adjacent levels of the device and is attached to adjacent levels by one or more sliding members or features. The sliding features may help prevent the neighboring levels from tilting and may help guide the levels so that they move in a desired direction relative to one another. One or more retaining features (e.g. hard stops, soft stops that transition to hard stops, frictional stops, non-releasable latching stops, releasable latching stops) may prevent adjacent levels from separating after expanding to their furthest positions relative to their adjacent cells. In the case of arrays, each cell can be attached to one or more corresponding elements of neighboring cells so they can move together or they may remain separate so they can move independently. Some or all unit cells may have wall, ceiling or open frame elements that have features to retain drugs or other biological or physiological materials of interest to a given application (e.g. cell growth). Individual elements may include different materials of biological interest to promote different activity at different levels or locations on a given level. Adjacent levels or cells may be joined by together by compliant elements (e.g. springs) so that movement of one brings a force to bear on adjacent elements without necessarily dictating conjoined movement. Relative movement of levels may engage spring latches with linear steps or ratcheting mechanisms, screw mechanisms (either of the releasable type or unreleasable type) such that movement, even possibly vibration, temperature change, magnetic or electrical force, leads to stepwise or continuous expansion without intervening periods of collapse. Some, though not all, preferred fabrication methods include multi-layer, multi-material electrochemical fabrication methods such as those practiced by Microfabrica with devices sizes in the microscale to millimeter scale range and with expansion factors that maybe two, five, ten, or even twenty times or more of the contracted size of the device.

During delivery of a device (whether or the cell or array type), the device may be in its as fabricated configuration, in a configuration that is further contracted than its fabrication configuration, in a configuration that is partially expanded, or in a configuration that is fully expanded. Devices may be utilized in vitro applications, used initially in vitro applications and then after some tissue growth moved into an in vivo environment, or may be directed used in in vivo applications.

Figure 2A:
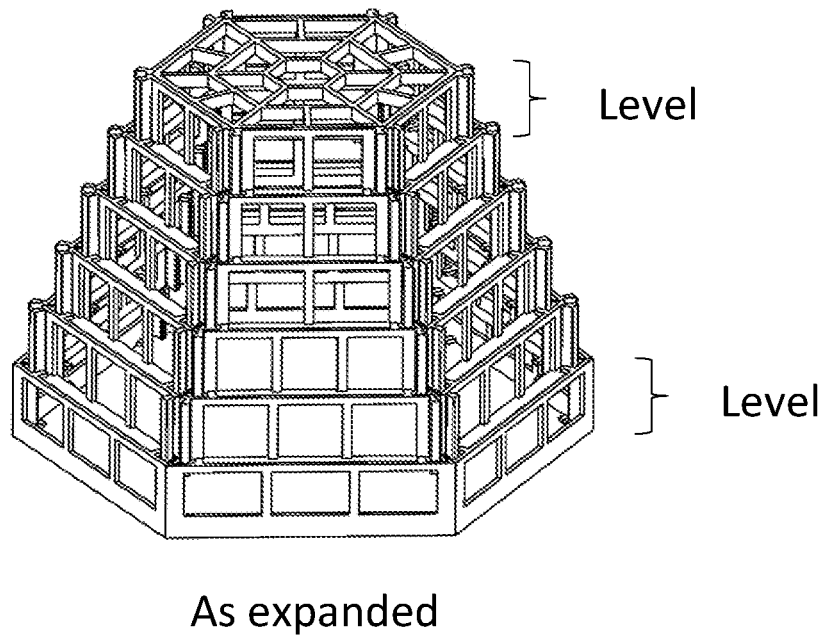
FIGS. 2A and 2B provide perspective views of an expandable sliding hexagonal scaffold device according to a first embodiment of the invention with the device comprising an open frame structure as shown in an expanded configuration in FIG. 2A and a collapsed and as formed configuration in FIG. 2B.
Figure 2B:
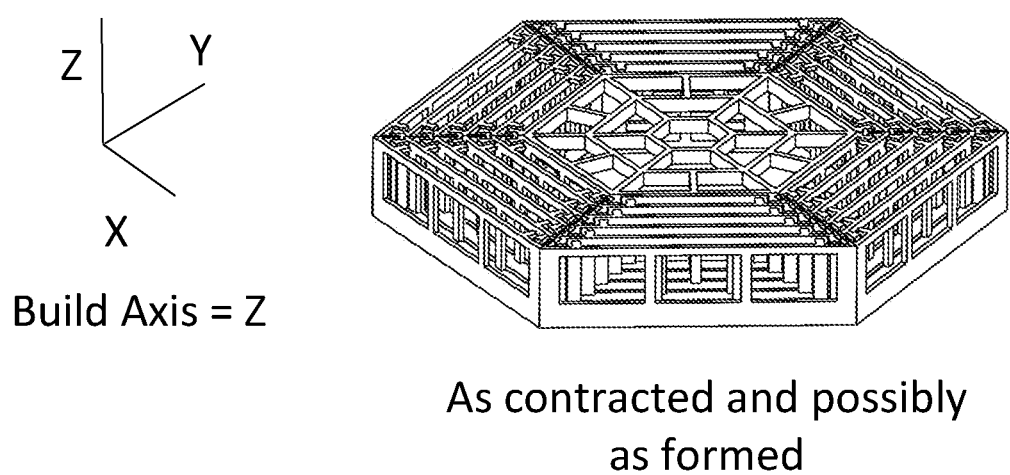

FIGS. 2A and 2B provide perspective views of an expandable sliding hexagonal scaffold device according to a first embodiment of the invention with the device shown in an expanded configuration in FIG. 2A and a collapsed, and possibly as formed, configuration in FIG. 2B. The device can be formed from a plurality of stacked layers with layer stacking occurring along the Z-axis and with lateral features, i.e. cross-sectional features, defined in X and Y space at different heights (for each layer) along the Z-axis. As shown, the example device of FIGS. 2A and 2B is made up of six movable (i.e. slidable) generally hexagonal elements that have configurations that allow sliding of the elements along the Z-axis.

Figure 2C:
FIGS. 2C and 2D provide close up perspective views of the slide channels, slide guide features, and slide stop features that control the extent of movement of each element or stage of the expandable scaffold device of FIGS. 2A and 2B.
Figure 2D:
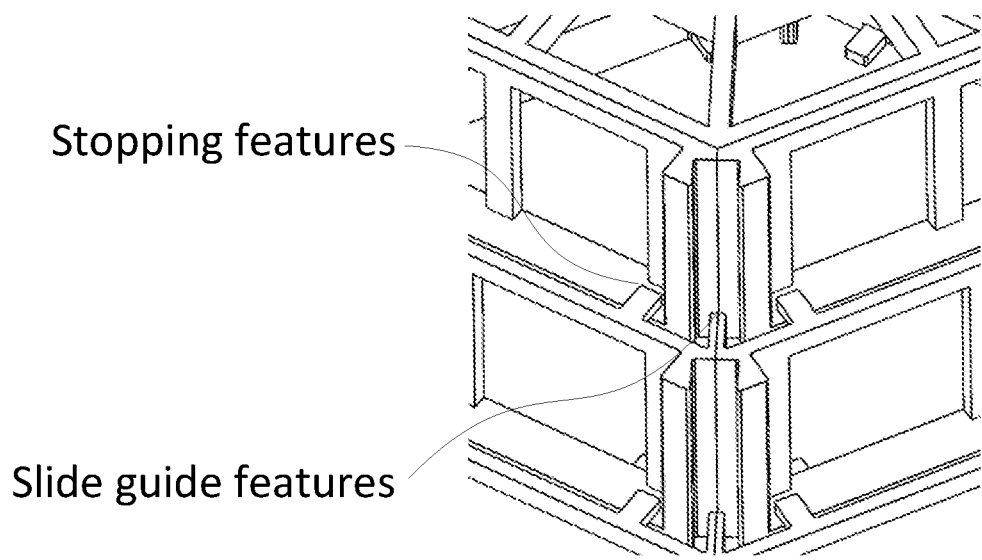

FIGS. 2C and 2D provide close up perspective views of the slide channels, slide guide features, and slide stop features that control the extent of movement of each element or stage of the expandable scaffold device of FIGS. 2A and 2B.

Figure 2E:
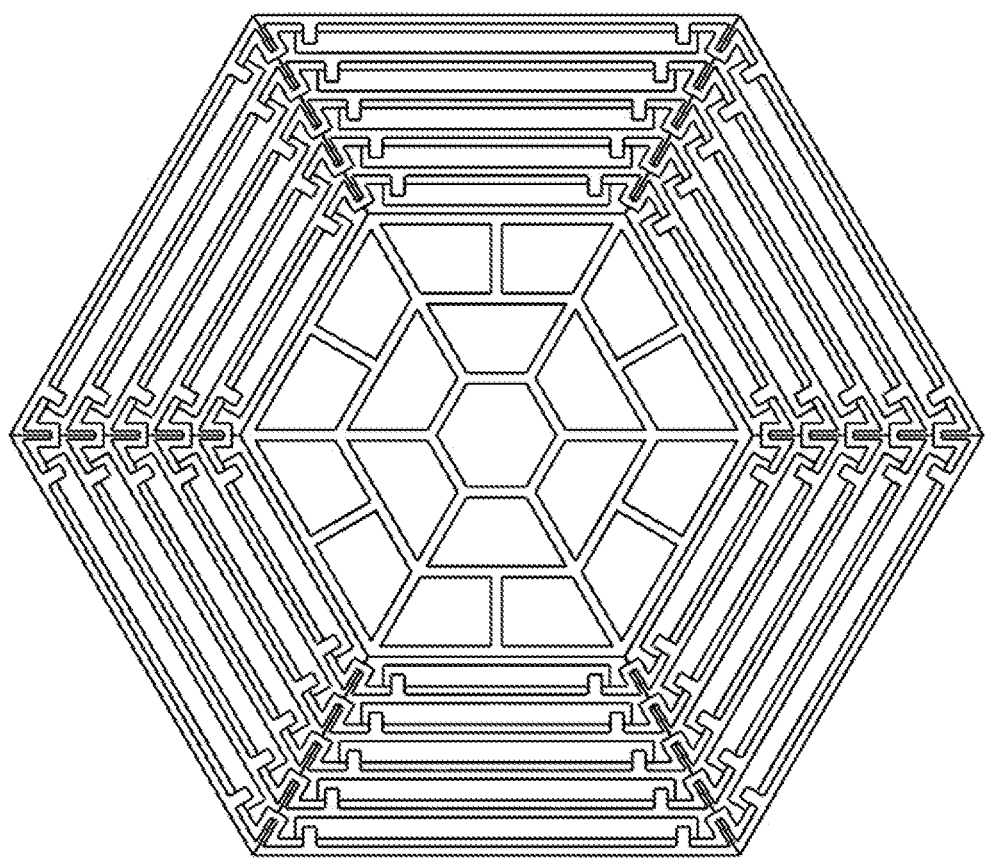
FIG. 2E provides a top view of the scaffold device of FIGS. 2A-2D wherein the individual elements or stages of the device can be seen along with the slide channels, slide guides, and stop features.

FIG. 2E provides a top view of the scaffold device of FIGS. 2A-2D wherein the individual elements or stages of the device can be seen along with the slide channels, slide guides, and stop features.

Numerous alternatives to the device embodiment of FIGS. 2A-2E, are possible and include for example, scaffolding devices with: (1) different numbers of expandable levels, (2) expandable levels of different individual heights, (3) levels that have other than regular hexagonal configurations, (4) levels that have tensioned or compressed spring elements that promote or inhibit expansion, (5) levels that individually have more complex geometric configurations, (6) levels formed of biocompatible materials (e.g. palladium, platinum, titanium, rhodium), (7) levels formed of non-biocompatible materials but provided with coatings that provide bio-compatibility, (8) levels that are formed of different materials, have coatings or pockets of different materials, or have different porosities extending there through to provide desired biological results (e.g. tissue growth, inhibition of tissue growth, orientation of fiber formation, and the like), (8) use of different stop features, (9) use of alternative linear channel or guide configurations (e.g. guides that have extended vertical elements or sliding spring configurations that provide for tilt inhibition) and/or (10) levels that are formed separately and then assembled prior to use.

Figure 3A:
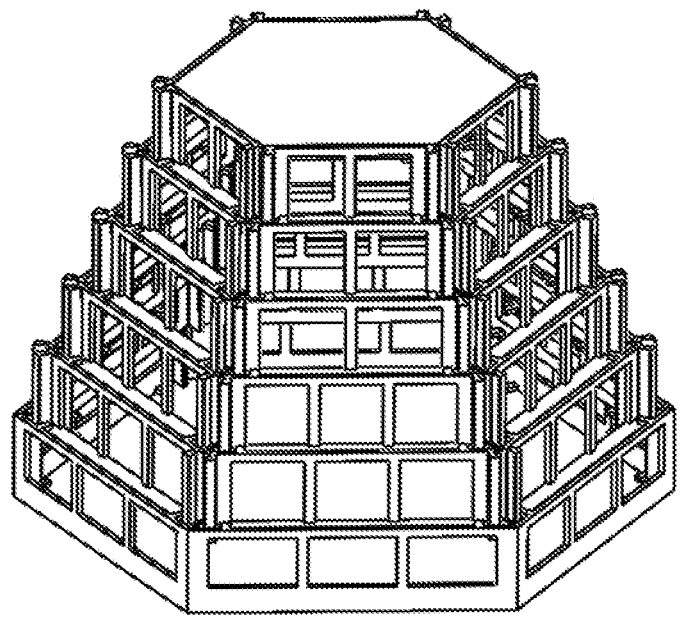
FIGS. 3A and 3B provide perspective views of an expandable sliding hexagonal scaffold device according to a second embodiment of the invention with the device comprising an open frame structure on the sides and a closed lid on the top as shown in an expanded configuration in FIG. 3A and a collapsed and as formed configuration in FIG. 3B.
Figure 3B:
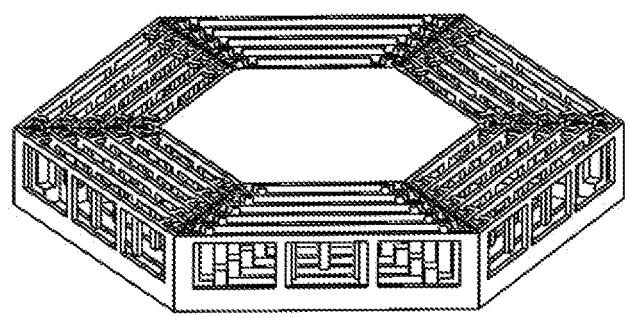

FIGS. 3A and 3B provide perspective views of an expandable sliding hexagonal scaffold device according to a second embodiment of the invention with the device comprising an open frame structure on the sides and a closed lid on the top as shown in an expanded configuration in FIG. 3A and a collapsed and possibly as formed configuration in FIG. 3B.

Figure 4A:
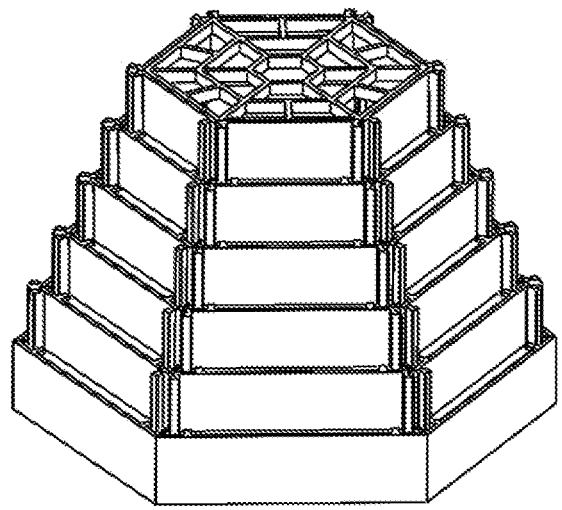
FIGS. 4A and 4B provide perspective views of an expandable sliding hexagonal scaffold device according to a third embodiment of the invention with the device comprising an open frame structure on the top and solid side walls as shown in an expanded configuration in FIG. 4A and a collapsed and as formed configuration in FIG. 4B.
Figure 4B:
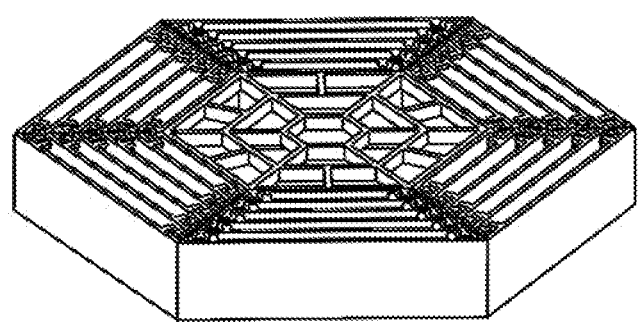

FIGS. 4A and 4B provide perspective views of an expandable sliding hexagonal scaffold device according to a third embodiment of the invention with the device comprising an open frame structure on the top and solid side walls as shown in an expanded configuration in FIG. 4A and a collapsed, and possibly as formed configuration in FIG. 4B.

Figure 5A:
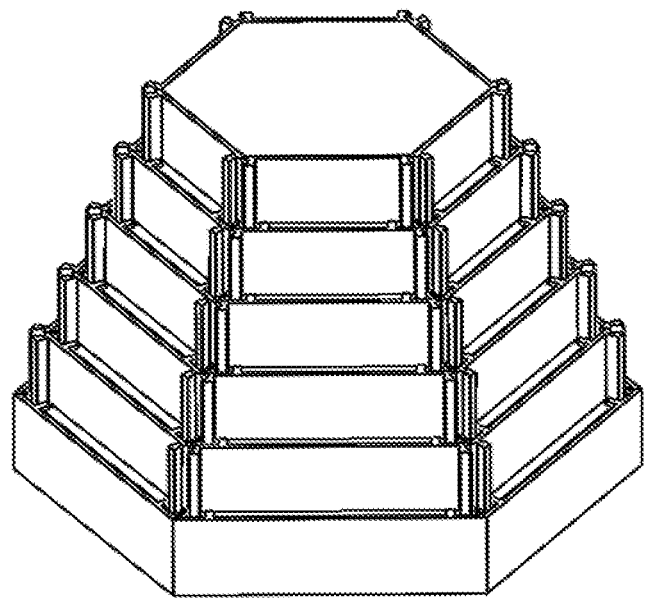
FIGS. 5A and 5B provide perspective views of an expandable sliding hexagonal scaffold device according to a fourth embodiment of the invention with the device comprising an solid lid on top and solid side walls as shown in an expanded configuration in FIG. 5A and a collapsed and as formed configuration in FIG. 5B.
Figure 5B:
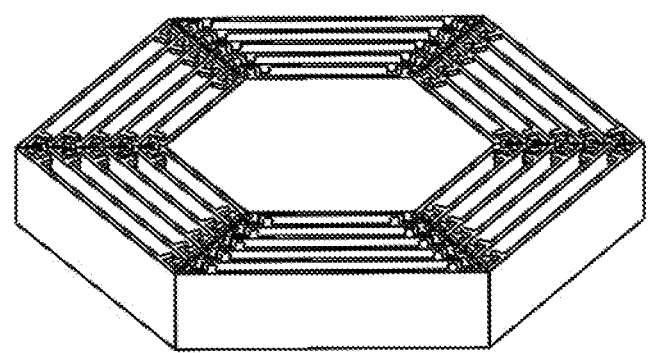

FIGS. 5A and 5B provide perspective views of an expandable sliding hexagonal scaffold device according to a fourth embodiment of the invention with the device comprising an solid lid on top and solid side walls as shown in an expanded configuration in FIG. 5A and a collapsed and as possibly as formed configuration in FIG. 5B.

Figure 6A:
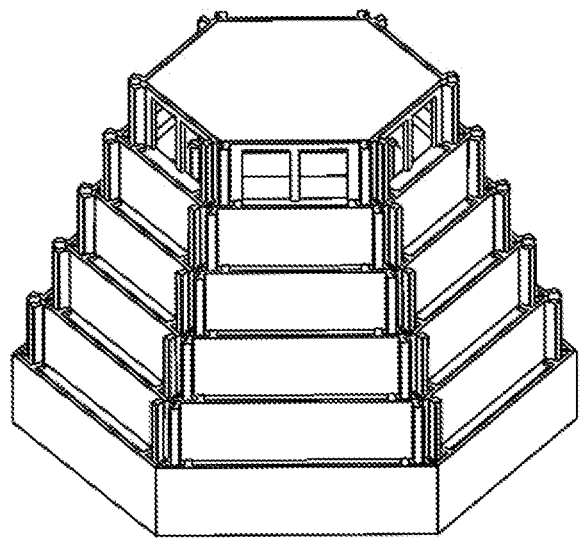
FIGS. 6A and 6B provide perspective views of an expandable sliding hexagonal scaffold device according to a fifth embodiment of the invention with the device comprising a solid lid on top and solid side walls with the exception of the side walls of the inner and upper most hexagonal element which has sides walls defined by an open frame configuration as shown in an expanded configuration in FIG. 6A and a collapsed and as formed configuration in FIG. 6B.
Figure 6B:
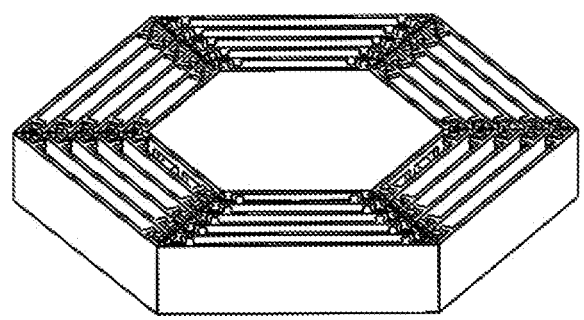

FIGS. 6A and 6B provide perspective views of an expandable sliding hexagonal scaffold device according to a fifth embodiment of the invention with the device comprising an solid lid on top and solid side walls with the exception of the side walls of the inner and upper most hexagonal element which has sides walls defined by an open frame configuration as shown in an expanded configuration in FIG. 6A and a collapsed and possibly as formed configuration in FIG. 6B.

As with the first embodiment, numerous variations of the second-fifth embodiments are possible and include the variations noted above for the first embodiment as well additional alternatives specifically directed to variations of the features specific to those embodiments.

Figure 7A:
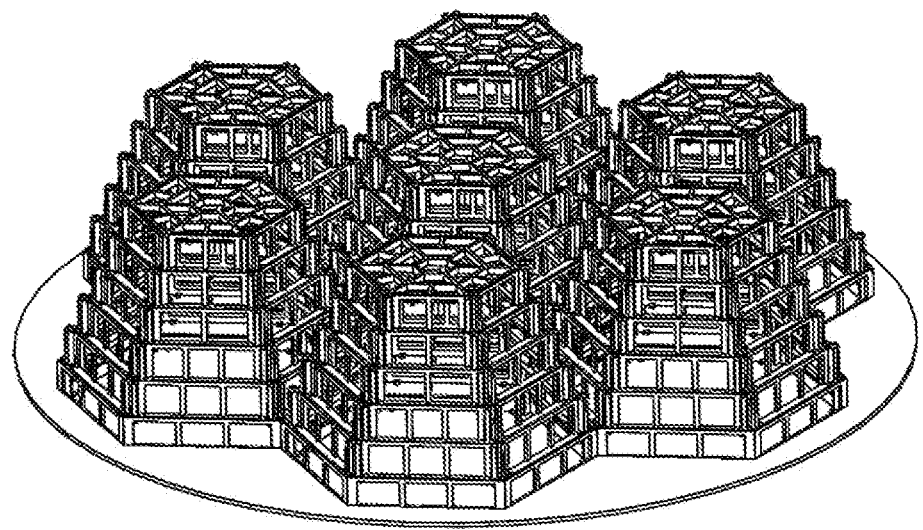
FIGS. 7A and 7B provide perspective views of an array of expandable sliding hexagonal scaffolding devices according to a sixth embodiment of the invention with each scaffolding device similar to that shown in FIGS. 2A-2E.
Figure 7B:
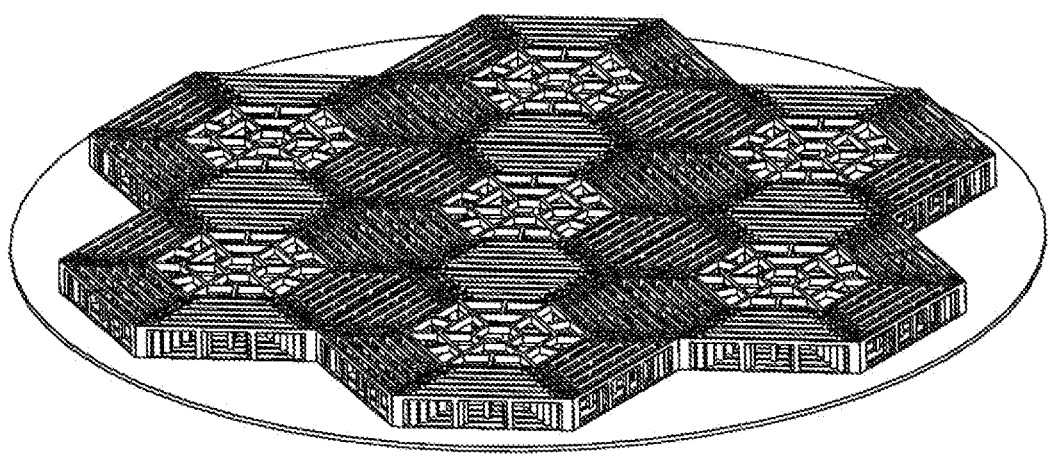

FIGS. 7A and 7B provide perspective views of an array of expandable sliding hexagonal scaffolding devices according to a sixth embodiment of the invention with each scaffolding device similar to that shown in FIGS. 2A-2E wherein FIG. 7A shows the array in expanded form while FIG. 7B shows the configuration in collapsed and possibly as fabricated configuration.

Various additional alternatives to the example expanding, sliding tissue scaffolds and arrays illustrated in FIGS. 2A-7B are possible, and include for example: (1) scaffold arrays may expand as an array of upside down pyramids as opposed to right side up pyramids; (2) scaffolding cells or arrays may be formed in stacks of two or more cells with each cell including a plurality of relatively movable elements; (3) arrays may be formed from adjacent cells with neighboring cells having alternating lateral expansion/contraction properties as vertical expansion occurs such that spacing between neighboring cells remains more consistent throughout the height of an expanded array; (4) a contracting array may be formed with some cells having their last level formed above other levels of the cells while adjacent expanding cells may be formed with their first levels formed below the other levels of the cells wherein the last levels of the adjacent cells are joined to one another such that upon vertical expansion of the adjacent cells each level of each cell ends up in proximity to or even engaged with (e.g. due upward extending feature on some levels of the expanding array and/or downward extending features on some levels of the contracting array) vertically adjacent levels of the neighboring cell or cells as vertical expansion occurs; (5) arrays formed of a plurality of cells being formed simultaneously and in their desired relative positions; (6) arrays formed of a plurality of cells either simultaneously or separately and then assembled into their desired configurations; (7) assembly of individual elements of individual cells may occur in right side up or upside down configurations as appropriate; (8) side and ceiling elements may take on other configurations such as regular or irregular rectangles, triangles, or other polygons, or circles, ellipses or other non-polygonal configurations; and/or (9) cells and elements of cells may include not only outer wall, ceiling, or floor elements but also internal elements such as vertical structures that extend from the ceiling or floor elements or horizontal structures that extend from the wall elements that do not unduly inhibit vertical expansion.

Group 2 embodiments provide expanding platform scaffolds or scaffolds that expand or contract based on folds, bends, or rotation of sections or features of elements relative to other sections or features. In these embodiments, individual elements may be defined as a group of structural features that include one or more movable structures whose configuration, origination, and/or functionality are repeated in a defined order by one or more neighboring set of structures wherein the relative movement allow expansion or contraction of the scaffold as a whole. Attributes and alternatives of the scaffolds of these embodiments are similar, mutatis mutandis, to those set forth above with regard to the first group of embodiments.

Figure 8A:
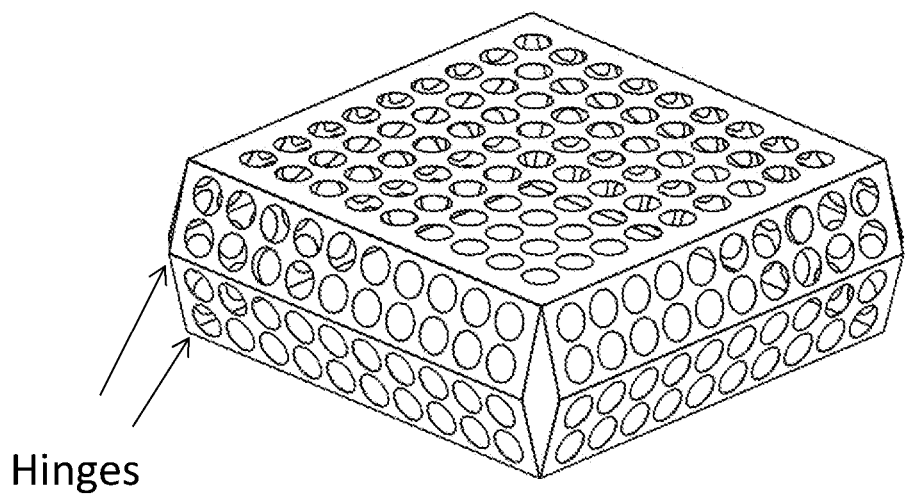
Figure 8B:
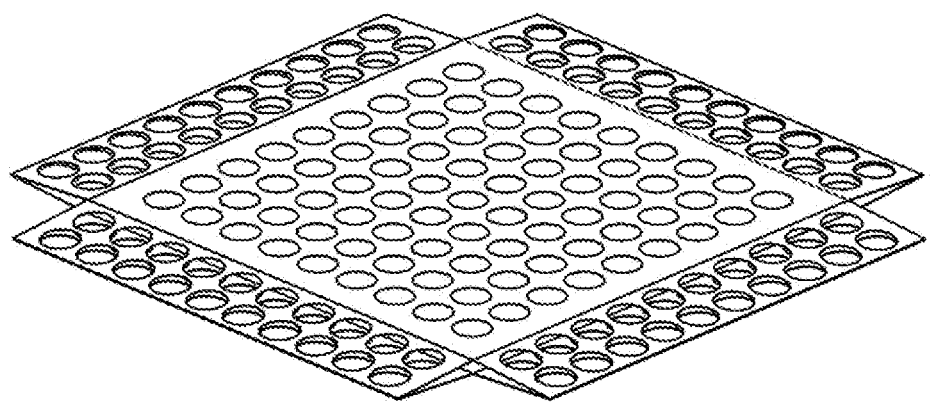

FIGS. 8A and 8B provide perspective views of an expandable, substantially rectangular, platform cell that may form a single cell expandable scaffolding device with side walls that fold outward from a collapsed position to an expanded position according to a seventh embodiment of the invention wherein FIG. 8A depicts the device in an expanded state while FIG. 8B depicts the device in a contracted or potentially as formed state.

Various alternatives to the cell configuration of FIGS. 8A and 8B are possible and include for example: (1) cells having configurations other than the illustrated substantially rectangular configuration, such as triangles, hexagons, and other regular or irregular polygons; (2) cells having different expandable height to width ratios; (3) cells having different wall and ceiling configurations such as substantially solid walls or ceilings; (4) cells with walls or ceilings with different porosities, (5) cells with more than two folding sections; (5) cells with accordion-like side walls; (6) cells with bending or folding locations that have narrowed material thicknesses compared to other locations on the side walls; (7) cells with perforations in bending or folding regions; (8) cells with hinge elements (e.g. pins and knuckles) to allow relative bending of neighboring structural elements (e.g. leaves); (9) folding, bending, or hinged elements with rotational stops that inhibit movement beyond a desired position (e.g. a position necessary to achieve a fully expanded state); (10) folding, bending, or hinged elements with spring biasing; (11) folding, bending, or hinged elements with non-releasable or releasable latch mechanisms or ratcheting mechanisms that inhibit movement in inappropriate directions; (12) cells may be made to include features and or material that provide desired biological features or enhancements, such as biocompatibility, drug delivery, tissue growth promoters, and the like; and/or (13) cells with or without one or both ceilings and flood structural features.

Figure 9A:
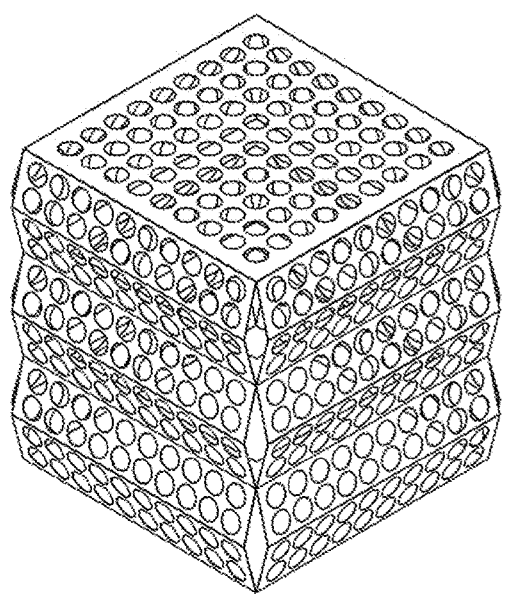
Figure 9B:
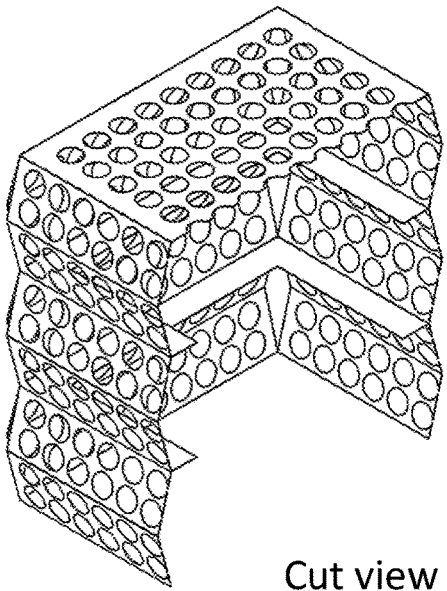
Figure 9C:
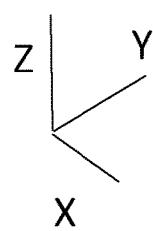
Figure 9C:
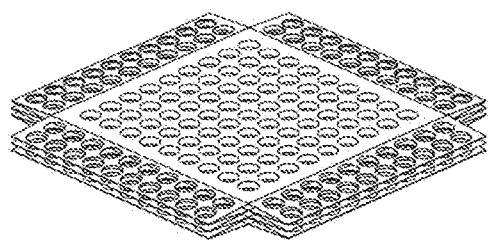

FIGS. 9A-9C provide perspective views of a three stage, expandable platform cell stack that may function as a multi-cell expandable tissue scaffolding device according to an eighth embodiment of the invention wherein individual cells are similar to that shown in FIGS. 8A and 8B with the exception that individual cells are separated, or joined, by a rectangular ring structure wherein FIG. 9A shows the device in an expanded state, FIG. 9B shows a cut view of the device in an expanded state, and FIG. 9C shows the device in a contracted, and possibly in an as fabricated, state.

Figure 10A:
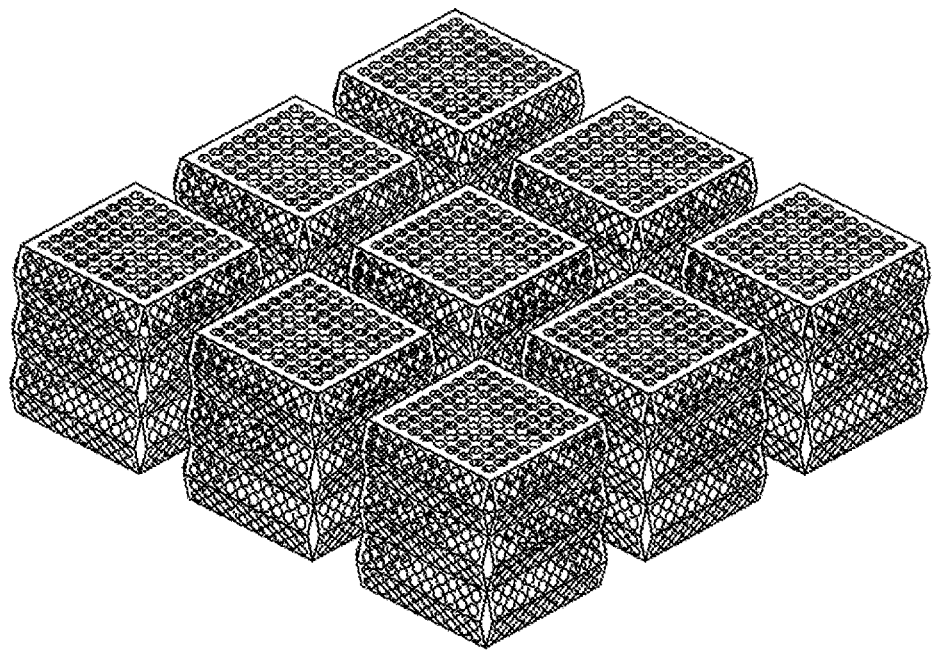
FIGS. 10A and 10B provide perspective views of a three by three array of three stage expandable platform scaffolding devices in an expanded state (FIG. 10A) and in a contracted, or possibly as fabricated state (FIG. 10B) according to a ninth embodiment of the invention with each scaffolding device similar to that shown in FIGS. 9A-9C.
Figure 10B:
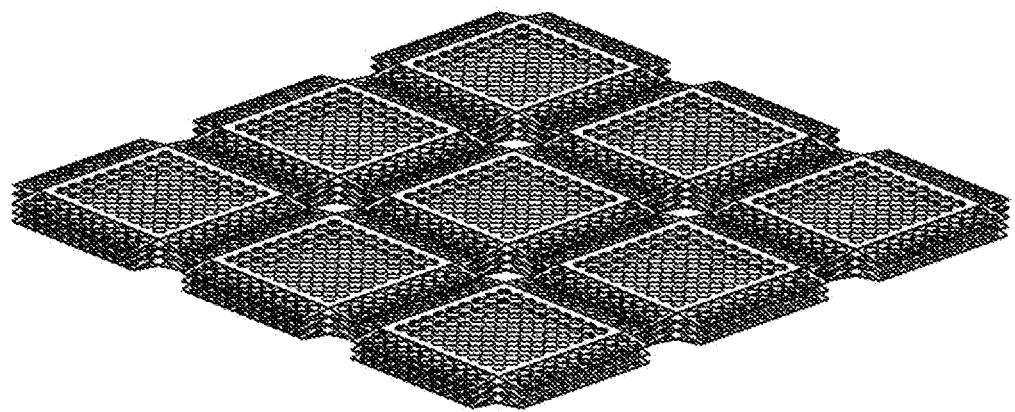

FIGS. 10A and 10B provide perspective views of a three-by-three array of three stage expandable platform scaffolding devices in an expanded state (FIG. 10A) and in a contracted, or possibly as fabricated, state (FIG. 10B) according to a ninth embodiment of the invention with each scaffolding device similar to that shown in FIGS. 9A-9C.

Figure 11A:
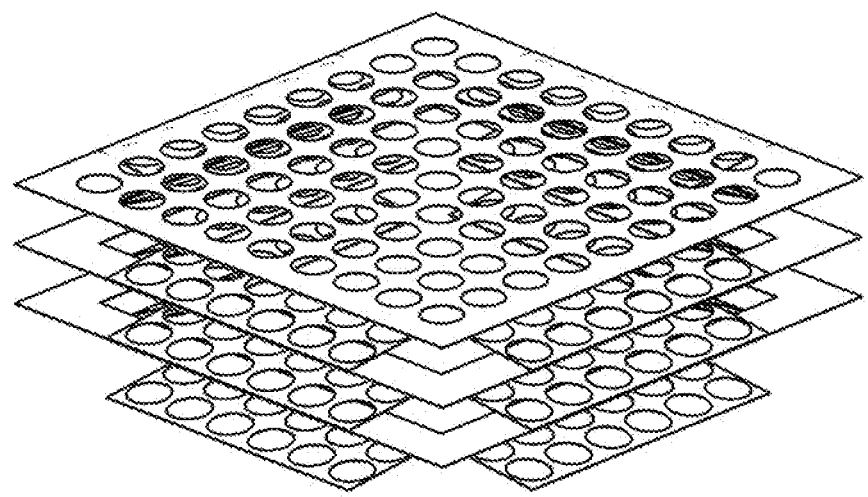
Figure 11B:
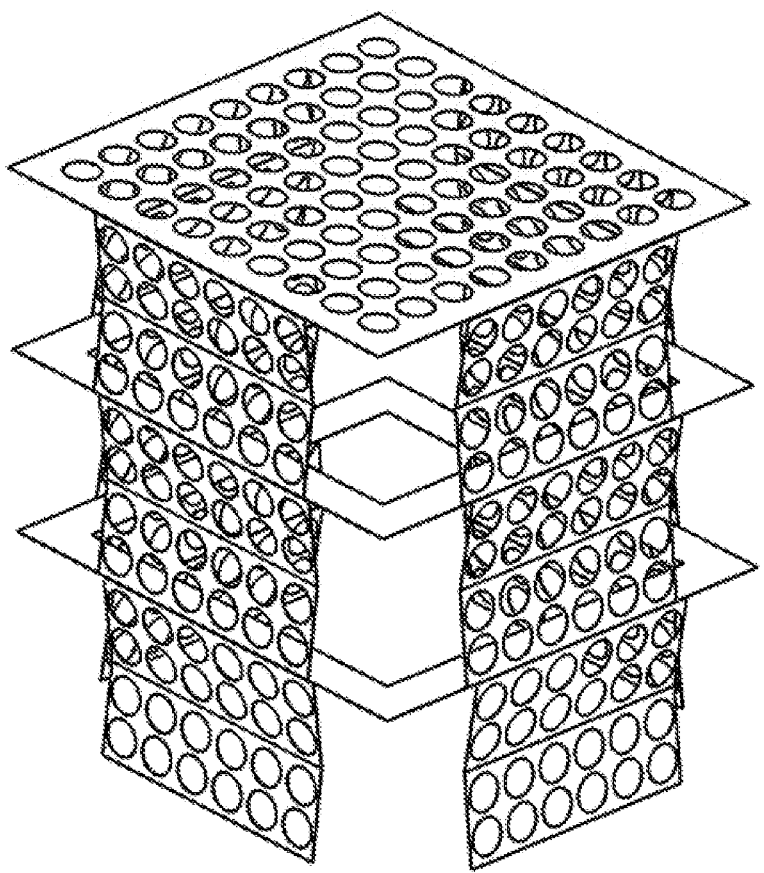

FIGS. 11A-11B provide perspective views of a three stage, expandable platform stack that may function as a multi-cell expandable tissue scaffolding device according to a tenth embodiment of the invention wherein individual cells have side walls that fold outward as expansion occurs wherein FIG. 11A shows the device in a contracted, and possibly in an as fabricated, state. FIG. 11B shows the device in an expanded state.

Figure 12A:
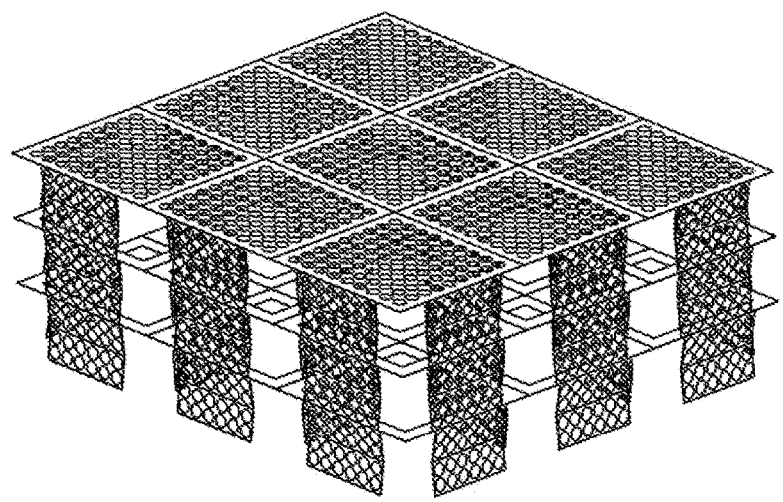
FIGS. 12A and 12B provide perspective views of a three by three array of three stage expandable platform scaffolding devices in an expanded state (FIG. 12A) and in a contracted, or possibly as fabricated, state (FIG. 12B) according to an eleventh embodiment of the invention with each scaffolding device similar to that shown in FIGS. 11A and 11B.
Figure 12B:
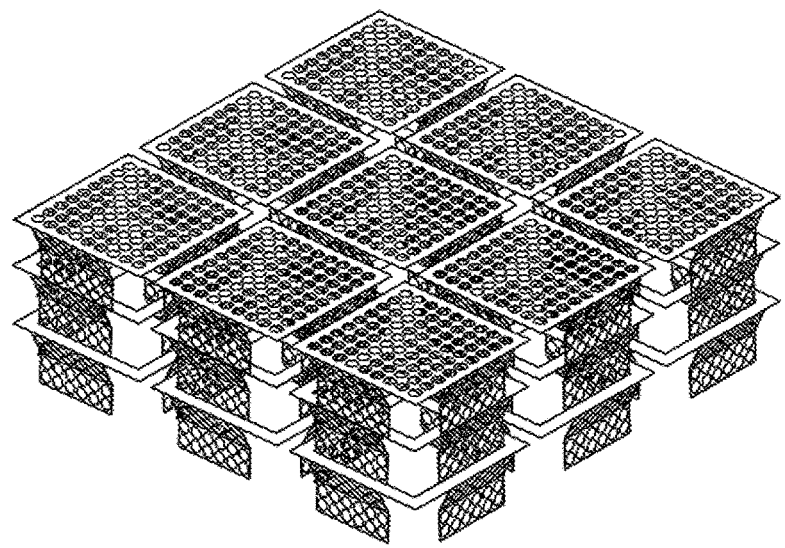

FIGS. 12A and 12B provide perspective views of a three by three array of three stage expandable platform scaffolding devices in an expanded state (FIG. 12A) and in a contracted, or possibly in an as fabricated, state (FIG. 12B) according to an eleventh embodiment of the invention with each scaffolding device being similar to that shown in FIGS. 11A and 11B.

Various additional alternatives to the example expanding platform scaffolds and scaffold arrays as illustrated in FIGS. 8A-12B are possible, and include for example: (1) wall patterns of the cells may take different configurations (other than patterns of circles) such as patterns of squares, open frames, horizontal lines, vertical lines, and the like; (2) individual walls may be divided into a plurality of wall segments; (3) scaffolds and array may include different numbers of stacked vertical cells and/or different numbers and arrangements of laterally displaced cells; and/or (4) scaffolds and arrays may consist of different types and combinations of cell types in both vertical and lateral positions.

Group 3 embodiments provide static scaffolds that do not substantially expand, contract, or change configuration, other than by loss of dissolvable features (e.g. drugs and/or other consumables), but are formed in their desired configurations, though in some embodiments, individual scaffolding elements may be stacked or laid adjacent one another to provide desired configurations. Features of these embodiments are similar to those noted for the group 1 and group 2 embodiments with the exception of those features related to sliding or other relative movement of elements. Cells can be patterned in the X-Y and Z directions. The shape of one unit cell can be hexagonal, square, triangle or any other shape that can nest. Each cell can be fabricated from a plurality of layers directly on top of one or more other cells or it can be assembled after fabrication. Each cell level can be attached to a level below it or beside it by laser welding, soldering, gluing or other similar processes. Each cell layer can be attached to a layer below it by using alignment features that can mechanically hold the layers together. These include clips or a feature, like a hole, that can be used in conjunction with a fastening device, like a wire. Each, or some, unit cells can have features to retain drugs or other biomaterials which may help in cell growth. Wall beams can be designed orthogonal with each other or at defined angles. Individual cells may be stacked in offset configurations or in aligned configurations.

Figure 13A:
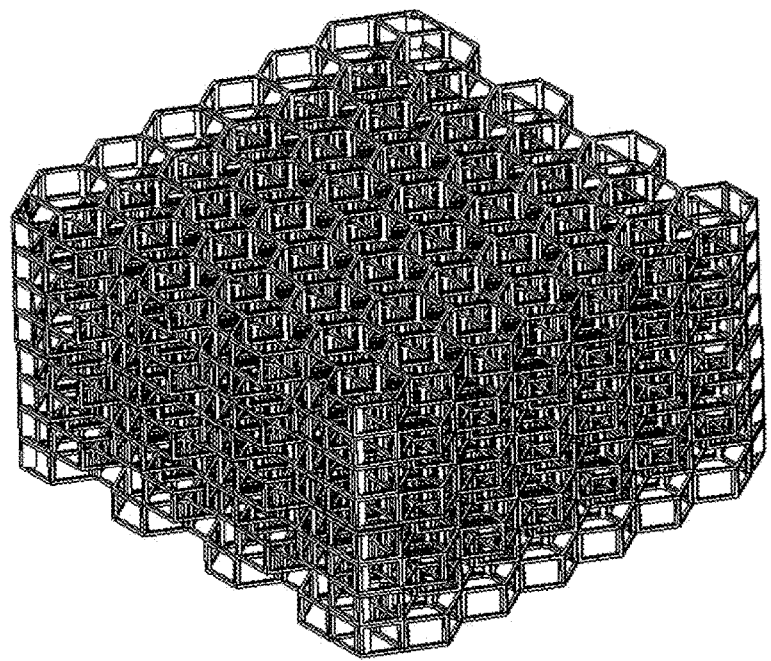
FIG. 13A provides a perspective view of a static or fixed size X by Y by Z multi-cell scaffolding structure according to a twelfth embodiment of the invention wherein individual cells are shifted in X and Y with alternative vertical cell levels.

[99] FIG. 13A provides a perspective view of a static or fixed size X by Y by Z multi-cell scaffolding structure according to a twelfth embodiment of the invention wherein individual cells are shifted in X and Y with alternating vertical cell level position (e.g. center of cells on one level are over cell corners from an adjacent level).

Figure 13B:
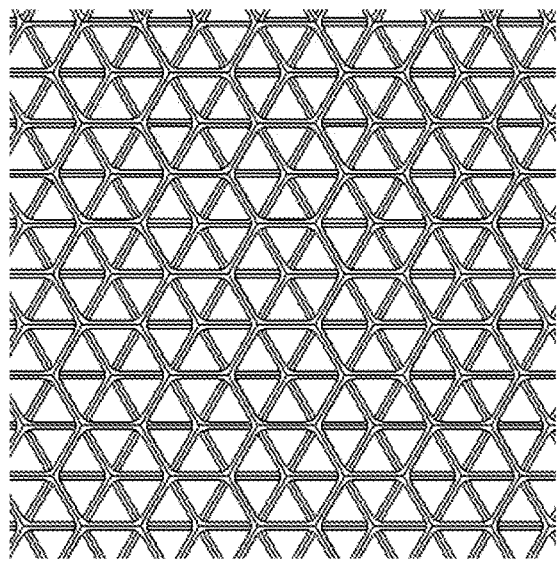
FIG. 13B provide a top view of the scaffolding structure of FIG. 13A wherein the shifting of the hexagonal cells in X and Y (with center locations of hexagons shifted to corner locations relative to adjacent vertical cell levels) can be more readily visualized.

FIG. 13B provides a top view of the scaffolding structure of FIG. 13A wherein the shifting of the hexagonal cells in X and Y (with center locations of hexagons shifted to corner locations relative to adjacent vertical cell levels) can be more readily visualized.

Figure 13C:
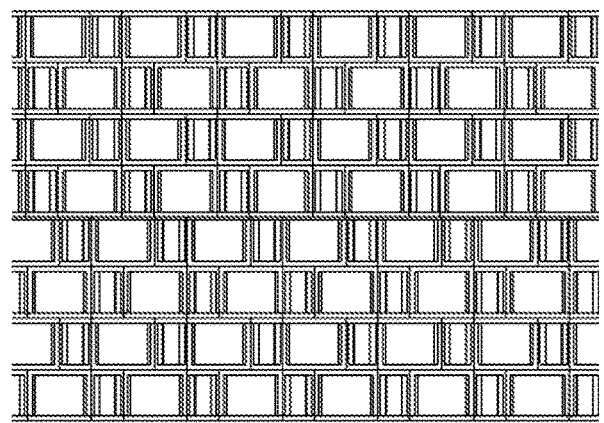
FIG. 13C provides a side view of the scaffolding structure of FIGS. 13A and 13B.

FIG. 13C provides a side view of the scaffolding structure of FIGS. 13A and 13B.

Figure 13D:
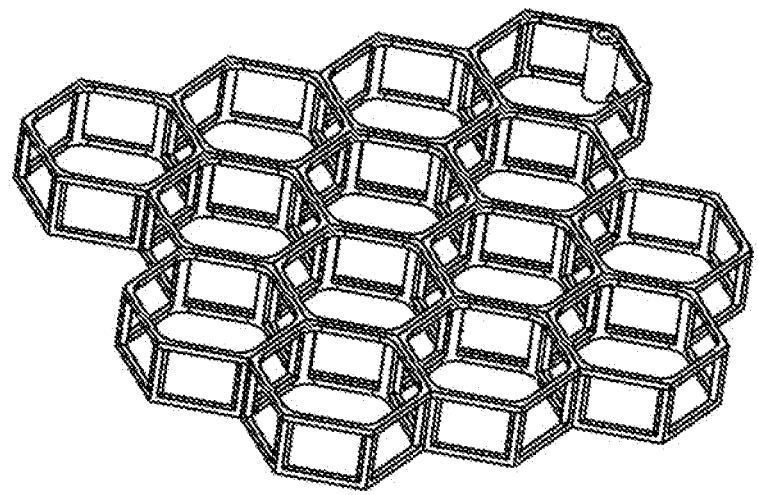
FIG. 13D provides a perspective view of one vertical level of a plurality of hexagonal cell structures that may be used as part of the structure of FIGS. 13A-13C.

FIG. 13D provides a perspective view of one vertical level of a plurality of hexagonal cell structures that may be used as part of the structure of FIGS. 13A-13C.

Figure 13E:
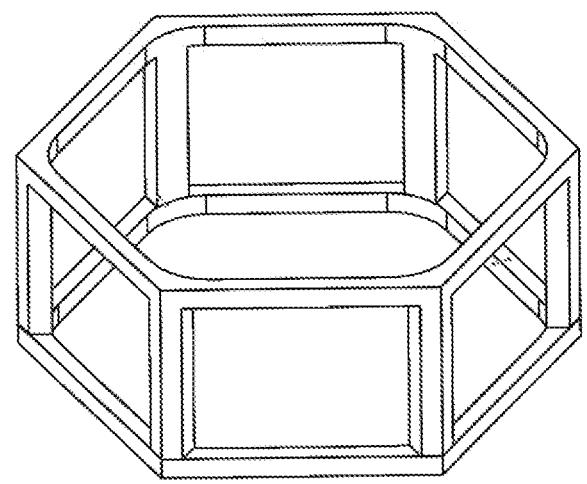
FIG. 13E provides a perspective view of a single hexagonal cell from which the structure of FIGS. 13A-13D may be formed where adjacent vertical frame bars and horizontal frame bars may be shared with adjacent cells when combined into an array.

FIG. 13E provides a perspective view of a single hexagonal cell from which the structure of FIGS. 13A-13D may be formed where adjacent vertical frame bars and horizontal frame bars may be shared with adjacent cells when combined into an array.

Figure 13F:
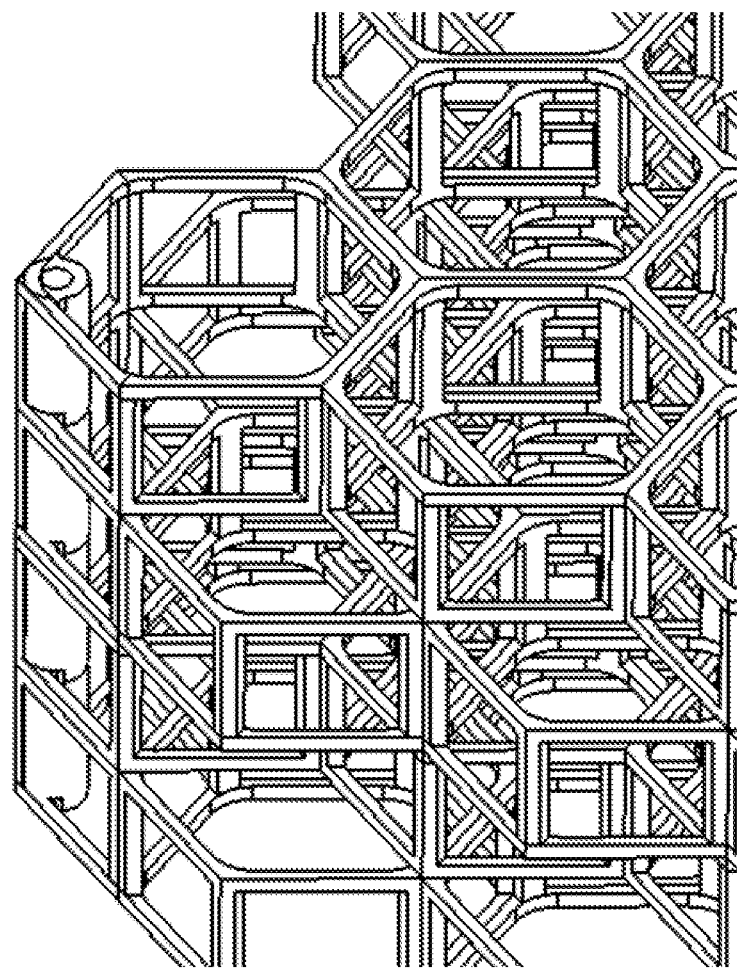
FIG. 13F provides a close up perspective view of a small number of stacked and horizontally arrayed hexagonal cells (similar to those forming the structure of FIGS. 13A-13E) along with an alignment feature that may be formed as part of the structure such that single levels of hexagonal cells may be formed and then stacked where careful examination indicates that the alignment feature is located in different positions relative to the hexagonal cells on alternating vertical levels.

FIG. 13F provides a close up perspective view of a small number of stacked and horizontally arrayed hexagonal cells (similar to those forming the structure of FIGS. 13A-13E) along with an alignment feature that may be formed as part of the structure such that single levels of hexagonal cells may be formed and then stacked where careful examination indicates that the alignment feature is located in different positions relative to the hexagonal cells on alternating vertical levels.

Various additional alternatives to the example static scaffolds of FIGS. 13A-13F are possible and include for example: (1) the variations noted with regard to the first and second groups of embodiments that do not involve moving features; (2) use of fewer or greater numbers of cell levels; (3) use of few or greater numbers of laterally positioned cells; (4) use of cells of different configurations within a single scaffolding device; (5) use of scaffolding structures that have varying heights and/or varying lateral dimensions and/or varying structural feature placement, orientation, or placement; (6) use of scaffolding structures that including material coatings or incorporate different materials in different regions (e.g. to provide biocompatibility, to provide selected drug delivery, and/or or to provide other biological or physiological functionality of interest).

Tissue scaffolding devices of the various embodiments may be used in a variety of applications and with a variety of tissues and material types including, but not limited to, for example: (1) bone; (2) tissue; (3) cartilage; (4) blood vessels; (5) bladder; (6) skin; (7) muscle; (8) stem cells; (9) organs; (10) drugs; (11) growth factors; (12) ligament; (13) bio adhesives; (14) nerves; (15) tendons; (16) BMP (bone morphogenic protein); and/or (17) HA (hydroxyl appetite).

In some applications, the scaffolding structures may not only provide structural integrity to growing tissue but also a desired configuration. Expandable scaffolds may also influence the direction of cell/fiber growth.

In applications involving expanding scaffolds, expansion may be controlled in a variety of different ways, including for example: (1) by pulling a string or wire that is connected to the scaffold; (2) by triggering a latch that holds the scaffold in a contracted state against a spring force which is allowed to expand the scaffold upon release of the latch; (3) in some embodiments a ratcheting mechanism or escapement mechanism may limit the amount of expansions upon each trigger event such that a scaffold may be expanded at any desirable rate varying from seconds, to minutes, hours, or even days; (4) in some applications, a spring force may need to be overcome to move the scaffold from a contracted state to an expanded state; or (5) in some applications, a delivery state may be somewhat larger or smaller than a fabrication state wherein expansion can occur after delivery is completed.

In one embodiment, a scaffolding structure of one of the three groups may be used in a dental application or in a spinal application where bone growth is desired. In such an application the scaffold may be inserted into a desired target region of a patient's body. The scaffold may be expanded after delivery, if not delivered in an expanded state. The scaffold may then be packed with BPM, alone or in combination with desired materials. The region may be then closed and bone growth allowed to occur. In the case of a dental application, after some months of bone growth, the restructured area can be used to receive a dental implant.

In another application, the scaffolding structure may be used to initially support desired articular cartilage growth in an in vitro environment from a patient's own cartilage. After sufficient growth has occurred, the cartilage and embedded scaffolding can be planted into the patient to provide improved functionality (e.g. in the knee).

In some embodiments, the growth of cells may provide the motive force for expanding a scaffolding structure. In some embodiments, a scaffold may initially have thickness on the order of 10s to 100s of microns and after expansion it may exceed 2, 5, 10, 20, or even 50 times its original height and be filled with and/or surrounded by desired tissue.

combined with the teachings of the instant application in many ways: For example, enhanced methods of producing structures may be derived from some combinations of teachings, enhanced structures may be obtainable, enhanced apparatus may be derived, and the like.

| U.S. Pat. application No., Filing Date U.S. application Pub No., Pub Date U.S. Pat. No., Pub Date | Inventor, Title |
|---|---|
| 10/830,262 - Apr. 21, 2004 2004-0251142A - Dec. 16, 2004 7,198,704 - Apr. 3, 2007 | Cohen, "Methods of Reducing Interlayer Discontinuities in Electrochemically Fabricated Three-Dimensional Structures" |
| 10/697,597 - Dec. 20, 2002 2004-0146650A - Jul. 29, 2004 | Lockard, "EFAB Methods and Apparatus Including Spray Metal or Powder Coating Processes" |
| 10/607,931- Jun. 27, 2003 2004-0140862 - Jul. 22, 2004 7,239,219 - Jul. 3, 2007 | Brown, "Miniature RF and Microwave Components and Methods for Fabricating Such Components" |
| 10/434,294 - May 7, 2003 2004-0065550A - Apr. 8, 2004 | Zhang, "Electrochemical Fabrication Methods With Enhanced Post Deposition Processing" |
| 10/841,006 - May 7, 2004 2005-0067292 - May 31, 2005 | Thompson, "Electrochemically Fabricated Structures Having Dielectric or Active Bases and Methods of and Apparatus for Producing Such Structures" |
| 10/841,347 - May 7, 2004 2005-0072681 - Apr. 7, 2005 | Cohen, "Multi-step Release Method for Electrochemically Fabricated Structures" |
| 11/506,586 - Aug. 8, 2006 2007-0039828 - Feb. 22, 2007 7,611,616 - Nov. 3, 2009 | Cohen, "Mesoscale and Microscale Device Fabrication Methods Using Split Structures and Alignment Elements" |
| 10/949,744 - Sep. 24, 2004 2005-0126916 - Jun. 16, 2005 7,498,714 - Mar. 3, 2009 | Lockard, "Three-Dimensional Structures Having Feature Sizes Smaller Than a Minimum Feature Size and Methods for Fabricating" |
| 12/345,624 - Dec. 29, 2008 — 8,070,931 - Dec. 6, 2011 | Cohen, "Electrochemical Fabrication Method Including Elastic Joining of Structures" |
| 10/995,609 - Nov. 22, 2004 2005-0202660 - Sep. 15, 2005 — | Cohen, "Electrochemical Fabrication Process Including Process Monitoring, Making Corrective Action Decisions, and Taking Appropriate Actions" |
| 11/029,218 - Jan. 3, 2005 2005-0199583 - Sep. 15, 2005 7,524,427 - Apr. 28, 2009 | Cohen, "Electrochemical Fabrication Methods Incorporating Dielectric Materials and/or Using Dielectric Substrates" |
| 12/906,970 - Oct. 18, 2010 2011-0132767 - Jun. 11, 2009 8,613,846 - Dec. 24, 2013 | Wu, "Multi-Layer, Multi-Material Fabrication Methods for Producing Micro-Scale and Millimeter-Scale Devices with Enhanced Electrical or Mechanical Properties" |
| 12/828,274 - Jun. 30, 2010 — 8,262,916 - Sep. 11, 2012 | Smalley, "Enhanced Methods for at least Partial In Situ Release of Sacrificial Material From Cavities or Channels and/or Sealing of Etching Holes During Fabrication of Multi-Layer Microscale or Millimeter-scale Complex Three-Dimensional Structures" |
| 14/280,517 May 16, 2014 — — | Cohen, "Stacking and Bonding Methods for Forming Multi-Layer, Three-Dimensional, Millimeter Scale and Microscale Structures" |
| 14/333,476 - Jul. 14, 2014 2015-0021299 - Jan. 22, 2015 — | Jensen, "Batch Methods of Forming Microscale or Millimeter Scale Structures Using Electro Discharge Machining Alone or In Combination with Other Fabrication Methods" |
| 14/660,903 - Mar. 17, 2015 — — | Chen, "Methods of Forming Parts from One or More Layers of Deposited Material(s)" |
| 14/720,719 - May 22, 2015 — — | Veeramani, "Methods of Forming Parts Using Laser Machining" |
| 14/872,033 - Sep. 30, 2015 — — | Le, "Multi-Layer, Multi-Material Microscale and Millimeter Scale Batch Part Fabrication Methods Including Disambiguation of Good Parts and Defective Parts" |

In another application, tissue scaffolds may be used in microfracture surgery (e.g. in knee rebuilding procedures) where damaged tissue is removed, soft tissue is manipulated to provide fresh blood, the tissue scaffolding is inserted, and an area is covered with a blood patch such that cartilage growth is enhanced.

The patent applications and patents set forth below are hereby incorporated by reference herein as if set forth in full. The teachings in these incorporated applications can be Though various portions of this specification have been provided with headers, it is not intended that the headers be used to limit the application of teachings found in one portion of the specification from applying to other portions of the specification. For example, it should be understood that alternatives acknowledged in association with one embodiment or aspect, are intended to apply to all embodiments or aspects to the extent that the features of the different embodiments or aspects make such application functional and do not otherwise contradict or remove all benefits of the adopted embodiment or aspect. Various other embodiments of the present invention exist. Some of these embodiments may be based on a combination of the teachings herein set forth herein directly with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. An in vivo method for treating a patient, comprising:
   (a) providing a microscale, mesoscale, or millimeter scale expandable tissue scaffolding device, comprising:
      (i) at least one first element having a plurality of first side facing features that have a first height and first slots extending at least partway along said height and a joining structure that connects said side facing features;
      (ii) at least one second element having a plurality of second guide features that movably extend into said first slots of said first element, such that movement of the at least one second element relative to the first element is permitted in a direction parallel to the first height; and
      (iii) at least one first stop feature forming part of one or both of the first and second elements that engages the other of the first element or the second element upon relative movement of the first and second elements reaching a first limit such that the at least one first stop feature inhibits excess movement and separation of the first and second elements;
   (b) inserting the tissue scaffolding device into a target region in a body of the patient; and
   (c) after inserting the tissue scaffolding device into the target region of the body, causing the at least one second element to move relative to the at least one first element to provide an expanded tissue scaffolding device and allowing selected tissue of the patient to enter and grow inside an opening in the tissue scaffolding device so as to provide a repair or treatment for the patient.

2. The method of claim 1 wherein the second element of the tissue scaffolding device comprising a plurality of second side facing second features that have a second height and second slots extending at least partway along said second height and a joining structure that connects said second side facing features; wherein the tissue scaffolding device additionally comprises:
   (d) at least one third element having a plurality of second guide features that movably extend into said second slots of said second element, such that movement of the at least one third element relative to the second element is permitted in a direction parallel to the second height, and
   (e) at least one second stop feature forming part of one or both of the second and third elements that engages the other of the second element or the third element upon relative movement of the second and third elements reaching a second limit such that the at least one second stop feature inhibits excess movement and separation of the second and third elements.

3. The method of claim 1 wherein the tissue scaffolding device changes shape while material of interest is growing.

4. The method of claim 1 wherein the tissue scaffolding device is made to change shape from a contracted size to an expanded size after insertion into the target region.

5. The method of claim 1 wherein the tissue scaffolding device structure influences a shape of the tissue growth.

6. The method of claim 1 wherein the tissue scaffolding device structure limits a shape of the tissue as it grows.

7. The method of claim 1 wherein the tissue scaffolding device is delivered in contracted form through an opening in the body of the patient, and then expanded afterwards via motivation selected from the group consisting of: (a) by growth of tissue, (b) by random movement, and (c) by a surgeon.

8. The method of claim 1 wherein windows exist in side facing features of at least one of the first or second elements and help guide the tissue growth.

9. The method of claim 1 wherein the scaffolding elements comprise material selected from the group consisting of: (a) bio-material that promotes selected material growth, (b) material that provides biocompatibility, (c) material that inhibits undesired tissue growth, (d) material that provides a beneficial treatment for the patient, (e) a bioabsorbable material, and (f) a biodegradable material, and (g) a tissue seeding material or material that can aid in the seeding of tissue.

10. The method of claim 1 wherein the tissue scaffolding device provides structural integrity for the tissue that is growing within it.

11. The method of claim 1 wherein the tissue scaffolding device further comprises features selected from the group consisting of: (a) at least one anchoring feature, (b) at least one locking mechanism for holding the at least one first and second elements in an expanded state after movement of the at least one first and second elements away from one another, (c) at least one mechanism for inhibiting contraction of the device after expansion, and (d) at least one barb to aid in securing the device to a target location.

12. The method of claim 1 wherein the tissue scaffolding device has features that are optimized to work with a bioadhesive.

13. The method of claim 1 wherein the scaffolding device has at least two different materials that promote growth of different tissues.

14. The method of claim 1 wherein the tissue scaffolding device is capable of expanding in multiple non-parallel directions.

15. The method of claim 1 wherein the tissue scaffolding device comprises controllably releasable drugs.

16. The method of claim 1 wherein the tissue scaffolding device comprises a metal and is fabricated using a multi-layer, multi-material electrochemical fabrication process.

17. The method of claim 1 wherein the tissue scaffolding device comprises an electronic component, selected from the group consisting of: (a) a pressure sensor; (b) an electronic component driven by one of: (i) pressure, (ii) electrical impulse, (iii) temperature, (iv) an RF signal, (v) electrochemical interaction, (vi) capacitance, and (vii) induction; (c) a piezoelectric device; (d) an electronic component that is operated in response to a closed loop signal; and (e) an electronic component that is operated in response to a periodic cycle within the body.

* * * * *